| United States Patent [19] | [11] Patent Number: 4,826,838 |
| --- | --- |
| Richardson et al. | [45] Date of Patent: May 2, 1989 |

[54] ANALGESIC CARBOCYCLIC AND HETEROCYCLIC CARBONYLMETHYLENE-AND CARBONYLMETHYPIPIDINES AND-PYRROLIDINES

[75] Inventors: Brian P. Richardson, Magden; Rudolf K. A. Giger, Riehen, both of Switzerland; Günter Engel, Weil, Fed. Rep. of Germany; Roland Furler, Therwil, Switzerland

[73] Assignee: Sandoz Ltd., Basel, Switzerland

[21] Appl. No.: 70,451

[22] Filed: Jul. 7, 1987

Related U.S. Application Data

[63] Continuation-in-part of Ser. No. 049,757, May 13, 1987, abandoned, which is a continuation of Ser. No. 815,617, Jan. 2, 1986, abandoned.

[30] Foreign Application Priority Data

| Jan. 7, 1985 [DE] | Fed. Rep. of Germany | 3500289 |
| Jan. 7, 1985 [DE] | Fed. Rep. of Germany | 3500290 |
| Feb. 27, 1987 [CH] | Switzerland | 759/87 |
| Mar. 6, 1987 [GB] | United Kingdom | 8705285 |

[51] Int. Cl.$^4$ .................... A61K 31/46; C07D 451/02

[52] U.S. Cl. .................... 514/210; 514/214; 514/294; 514/299; 514/304; 514/305; 540/582; 546/94; 546/112; 546/124; 546/126; 546/133; 546/129; 548/452; 548/454; 548/455; 548/453

[58] Field of Search .................. 546/94, 112, 124, 126, 546/129, 133; 548/452, 453, 454, 455; 540/582; 514/210, 214, 294, 299, 304, 305

[56] References Cited

U.S. PATENT DOCUMENTS

| 2,800,480 | 7/1957 | Zirkle | 546/124 |
| 3,857,848 | 12/1974 | Mauvernay et al. | 546/133 |

FOREIGN PATENT DOCUMENTS 897117 12/1983 Belgium .
67770 12/1982 European Pat. Off. .

*Primary Examiner*—Mary C. Lee
*Assistant Examiner*—Bernard L. Dentz
*Attorney, Agent, or Firm*—Gerald D. Sharkin; Robert S. Honor; Joseph J. Borovian

[57] ABSTRACT

Carbocyclic and heterocyclic carbonylmethylene- and carbonylmethylpiperidines and -pyrrolidines are serotonin antagonists.

17 Claims, No Drawings

ANALGESIC CARBOCYCLIC AND HETEROCYCLIC CARBONYLMETHYLENE-AND CARBONYLMETHYPIPIDINES AND-PYRROLIDINES

This is a continuation-in-part of Ser. No. 049,757, filed on May 13, 1987 now abandoned which in turn is a continuation of Ser. No. 815,617 filed Jan. 2, 1986, both now abandoned.

The present invention relates to novel carbocyclic and heterocyclic carbonylmethylene- and carbonylmethylpiperidines and -pyrrolidines, processes for their production, pharmaceutical compositions contaning them and their use as pharmaceuticals.

It has been proposed (see for example J. R. Fozard in Advances in Neurology Vol. 33 Raven Press New York 1982) to use compounds with serotonin antagonistic effects, i.e. 5-HT blocking effects, in the treatment of migraine. Particularly interesting are the compounds which antagonize the 5-HT$_3$ receptors. A particular active compound of this type is Metoclopramide (U.S. Pat. No. 3,177,252) which J. B. Hughes in Med. J. Australia 2 No. 17. p. 580 (1977) has reported to lead to an immediate beneficial effect on a migraine attack on slow i.v. injection of 10 mg.

Subsequently further compounds with 5-HT$_3$ antagonistic effect has been described. European Publication No. 67770 describes a narrow class of tropane phenyl esters.

Belgian Pat. No. 897 117 discloses benzene-, indene-, indole-, benzofurane- and benzothiophene-carboxylic acid piperidinyl esters and amides wherein the piperidinyl groups contain an alkylene bridge with 5-HT$_3$ receptor antagonish activity. These compounds are useful in the treatment of pain, as antiarrhythmics and antipsychotics.

The present invention provides a new group of compounds which has not been specifically suggested before in the literature and which have particularly interesting pharmacological properties, for example 5-HT$_3$ antagonistic and anti-arrhythmic activities, e.g. as indicated by potency in the vagus nerve test mentioned hereinafter. Furthermore the compounds are useful in the treatment of gastrointestinal disorders.

The present invention provides carbocyclic and heterocyclic carbonylmethylene- and carbonylmethylpiperidines and -pyrrolidines, which piperidine and pyrrolidine rings contain an alkylene bridge and are optionally unsaturated with the proviso that (i) when the piperidine ring containing an alkylene bridge signifies 3-tropanyl, the carbocyclic carbonylmethyl residue is not a benzoylmethyl group, and (ii) when the piperidine ring containing an alkylene bridge signifies the 3-quinuclidinyl group, the carbocyclic carbonylmethylene and carbonylmethyl residues are not benzoylmethyl and benzoylmethylene groups, as well as acid addition salts and quaternary ammonium salts thereof, hereinafter referred to as compounds of the invention. It is to be appreciated that the compounds of the invention may be optionally substituted in any available position.

In particular the present invention provides a compound of formula I,

A—CO—B    I wherein A is a group of formula II or III,

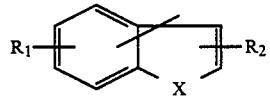
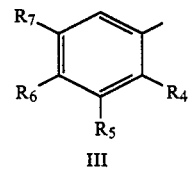

II     III wherein the free valence is attached to either fused ring in formula II, X is —CH$_2$—, —NR$_3$—, —O— or —S—, R$_1$ and R$_2$ independently are hydrogen, halogen, (C$_{1-4}$)alkyl, (C$_{1-4}$)alkoxy, hydroxy, amino, (C$_{1-4}$)alkylamino, di(C$_{1-4}$)alkylamino, mercapto or (C$_{1-4}$)alkylthio, and R$_3$ is hydrogen, (C$_{1-4}$)alkyl, (C$_{3-5}$)alkenyl, aryl or aralkyl, R$_4$ to R$_7$ independently are hydrogen, amino, nitro, (C$_{1-4}$)alkylamino, di(C$_{1-4}$)alkylamino, halogen, (C$_{1-4}$)alkoxy, (C$_{1-4}$)alkyl, (C$_{1-4}$)alkanoylamino or pyrrolyl, B is one of the groups of formula IV to XVIII,

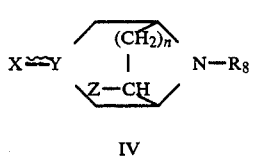
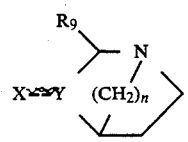

IV     V

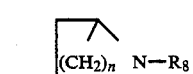
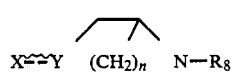

VI     VII

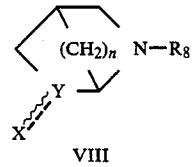
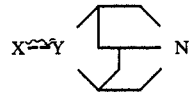

VIII     IX

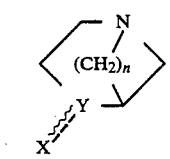
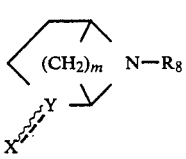

X     XI

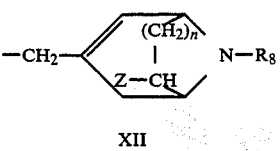
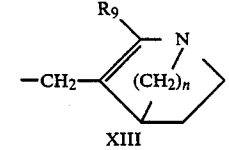

XII     XIII

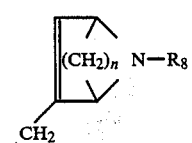
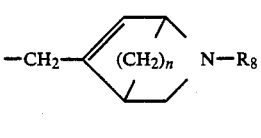

XIV     XV

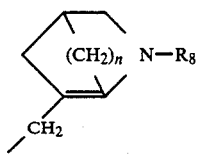 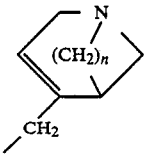

XVI  XVII

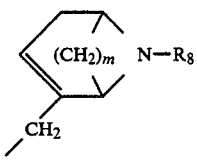

XVIII wherein n is 1, 2 or 3,

Z is hydrogen or $(C_{1-4})$alkoxy, $R_8$ is hydrogen, $(C_{1-7})$alkyl, $(C_{3-5})$alkenyl, aryl or aralkyl and X-Y is

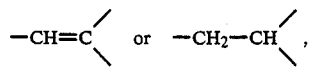

$R_9$ is hydrogen or $(C_{1-4})$alkyl, m is 2 or 3, the bond in group of formula X or XVII is in position 3 or 4, with the proviso that when A is a group of formula III, B is not a group of formula IV, wherein n is 1, Z is hydrogen, $R_8$ is methyl and X-Y is

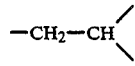

and not a group of formula V, wherein n is 2, $R_9$ is hydrogen and X-Y is

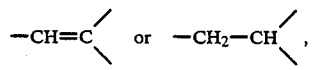

as well as acid addition and quaternary ammonium salts thereof.

One preferred group of compounds of formula I are those of formula Ia,

A—CO—B'  Ia wherein A is as defined above for formula I and B' is one of the groups IV to XI, wherein n, Z, $R_8$, $R_9$ and m are as defined for formula I and X-Y is

with the proviso that when A is a group of formula III, B' is not a group of formula V, wherein n is 2, and $R_9$ is hydrogen, as well as acid addition salts and quaternary ammonium salts thereof.

Another preferred group of compounds of formula I are those of formula Ib,

A—CO—B"  Ib wherein A is as defined for formula I and B" is one of the groups IV to XI, wherein n, Z, $R_8$, $R_9$ and m are as defined for formula I and X-Y is

and subject to the provisos given for formula I, as well as acid addition salts and quaternary ammonium salts thereof.

A further preferred group of compounds of formula I are those of formula Ic,

A—CO—B'''  Ic wherein A is as defined for formula I, and B''' is one of the groups XII-XVIII, wherein n, Z, $R_8$, $R_9$ and m are as defined for formula I, as well as acid addition salts and quaternary ammonium salts thereof.

Carbonylmethylen-piperidines and -pyrolidines e.g. compounds of formula I wherein X-Y is

occur as a mixture of diastereoisomers (geometric cis-/trans isomers). The geometric isomers can appear as racemates as well as individual enantiomers. The compounds of the invention include all possible individual enantiomers, racemic mixtures, diastereoisomers as well as mixtures thereof.

An alkyl moiety preferably is methyl, ethyl or propyl. Alkoxy is preferably methoxy or ethoxy. Aralkyl is convenient aryl$(C_{1-4})$alkyl. Alkenyl is preferably allyl or methallyl. An aryl moiety is preferably unsubstituted phenyl or phenyl mono- or poly-substituted by $(C_{1-4})$alkyl, e.g. methyl, halogen, e.g. fluorine, hydroxy, or $(C_{1-4})$alkoxy, e.g. methoxy. Preferably any substituted aryl group is mono-substituted. Aralkyl is conveniently benzyl. Halogen is fluorine, chlorine, bromine or iodine.

A is conveniently a group of formula II. In the group of formula II, the carbonyl side chain may be attached to the ring carbon atom in positions 2, 3, 4, 5, 6 or 7 of the nucleus, but preferably in position 3. Preferably A is indole or benzothiophene.

$R_1$ is attached to the ring carbon atom in position 4, 5, 6 or 12 of the nucleus, preferably in position 5 and $R_2$ is attached to the ring carbon atom in position 2 or 3 of the nucleus. Tautomers are also covered by formula I e.g. when $R_2$ is hydroxy or mercapto in the 2 position. $R_1$ is preferably hydrogen or halogen.

$R_2$ is preferably hydrogen or alkyl.

$R_8$ is preferably alkyl, especially methyl.

Preferred groups of formula III are of formula IIIa

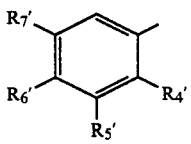
IIIa wherein $R_4'$ is $(C_{1-4})$alkoxy, especially methoxy, $R_5'$ is hydrogen, $R_6'$ is amino or $(C_{1-4})$alkylamino, especially methylamino, $R_7'$ is halogen, especially chlorine.

The moiety B may have two different configurations. The two different configurations may be appreciated by making the groups have a configuration wherein a reference plane may be drawn through the carbon atoms of the ring and the nitrogen atom is above the plane and the alkylene bridge is below the plane. A group of formula IV to XVIII has the α configuration when the group A—CO is below the plane on the same side as the alkylene bridge. This corresponds to the endo configuration and also to the configuration in tropine etc. A group of formula IV to XVIII has the β-configuration when it is above the plane on the same side as the nitrogen atom. This corresponds to the exo configuration and also the configuration is pseudotropine etc. Used hereinafter is the exo/endo nomenclature. The endo isomers are preferred.

The present invention furthermore provides a process for the production of a compound of the invention as well as acid addition salts thereof or quaternary ammonium salts thereof which includes the step of (a) reacting an appropriate carbocyclic or heterocyclic magnesium salt with an appropriate piperidylidene-methylene-carboxylic acid halide or a pyrrolidylidene-methylene-carboxylic acid halide, which piperidine and pyrrolidine rings contain an alkylene bridge under Grignard reaction conditions, or (b) optionally reducing the resulting compound or (c) optionally isomerizing the resulting compound of step (a) and recovering the obtained compound of the invention as such or as an acid addition salt or as a quaternary ammonium salt thereof.

In particular a compound of formula I as defined above or an acid addition salt or a quaternary ammonium salt thereof may be produced by a process which comprises (a) producing a compound of formula Ia

Ia wherein A and B' are as defined above, or an acid addition salt or a quaternary ammonium salt thereof, by reacting a compound of formula XIX

XIX wherein A is as defined above and hal is chlorine, bromine or iodine, with a compound of formula XX,

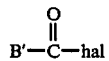
XX wherein B' and hal are as defined above, under Grignard reaction conditions, or (b) producing a compound of formula Ib

Ib wherein A and B" are as defined above, or an acid addition salt or a quaternary ammonium salt thereof, by reducing a compound of formula Ia, or (c) producing a compound of formula Ic

Ic wherein A and B'" are as defined above, or an acid addition salt or a quaternary ammonium salt thereof, by isomerizing a compound of formula Ia, wherein B' is one of the groups IV–VIII, X or XI, and recovering the obtained compound of formula I as such or as an acid addition salt or as a quaternary ammonium salt thereof.

Process (a) may be effected in conventional manner. The reaction is carried out in an inert organic solvent, such as diethylether or tetrahydrofuran. Suitable temperatures are from about −20° C., preferably from −20° to 0° C.

Process (b) may be effected in conventional manner for analogous reductions, for example by catalytic hydrogenation. Suitable catalysts include palladium-on-carbon. An inert organic solvent, e.g. ethanol, is suitably employed. The hydrogenation is conveniently effected at a temperature of from 20° to 30° C.

Process (c) may be performed in conventional manner for similar isomerization reactions. For example, a structurally appropriate compound e.g. a compound of formula Ia can be subjected to thermal treatment in absence of a solvent, optionally in vacuo. The preferred temperature values are from about 80° C. to about 100° C.

The carbocyclic or heterocyclic magnesium salt used as starting material for process (a) such as a compound of formula XIX can be prepared in known manner.

The piperidylidene-methylene-carboxylic acid halides or pyrrolidylidene-methylene-carboxylic acid halides e.g. a compound of formula XX, may be produced by reacting an appropriate piperidone or pyrrolidinone, which piperidine and pyrrolidine rings contain an alkylene bridge, with triphenylphosphincarbomethoxymethylene to produce the corresponding carboxylic acid methyl ester, which is converted via the carboxylic acid to the carboxylic acid halides.

A precursor of a starting material may be employed if desired. Such a precursor may be capable of being converted into the starting material in conventional manner but instead the process of the invention is carried out with the precursor and the other starting material or materials or a precursor thereof. The resultant product is converted into the compound of the invention in conventional manner, e.g. by using the same reaction conditions by which the precursor may be converted into the starting material. Typical precursors include protected forms of a starting material, e.g. wherein amino groups are temporarily protected.

Insofar as the production of any starting material is not particularly described herein, it is known, or may be produced in analogous manner to known compounds, in analogous manner to that described herein, e.g. the examples, or to known procedures for analogous compounds.

Any mixture of the exo and endo forms may be separated by chromatography.

Free base forms of compounds of the invention may be converted into salt forms. For example acid addition salts may be produced in conventional manner by reacting with a suitable acid, and vice versa. Suitable acids for salt formation include hydrochloric acid, malonic acid, hydrobromic acid, maleic acid, malic acid, fumaric acid, methanesulphonic acid, oxalic acid, and tartaric acid. Quaternary ammonium salts of the compounds of the invention may be produced in conventional manner, e.g. by reaction with methyl iodide.

In the following examples all temperatures are in degrees Centigrade and are uncorrected.

EXAMPLE 1

Indol-3-yl-carbonyl-methylenyl-3-(8-methyl-8-azabicyclo[3.2.1]octane)

[Compound of formula Ia, wherein A=II in 3-position; X=NH; $R_1=R_2=H$; B'=IV; X-Y is

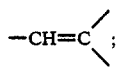

n=1; Z=H; $R_8=CH_3$]

(a)
8-Methyl-8-azabicyclo[3.2.1]octylidene-3-carbomethoxymethylene 76.5 g (0.225M) Triphenylphosphin-carbomethoxymethylen and 61 g (0.5M) benzoic acid are dissolved at 40° in 500 ml abs. benzene. A solution of 63 g (0.45M) 8-methyl-8-azabicyclo[3.2.1]octan-3-one (tropinone) in 100 ml abs. benzene is quickly added and the mixture heated under reflux for 18 hours. The mixture is partitioned between 2N $Na_2CO_3$ solution and $CH_2Cl_2$. The organic phase is evaporated, the residue is dissolved in $CH_2Cl_2$ and the solution is diluted to a 3-fold volume by addition of hexane. The precipitated solids (triphenylphosphinoxide) are filtered off and the filtrate is chromatographed on 25-fold amount of silica gel eluting with $CH_2Cl_2$ containing 10% $CH_3OH$ to remove 55 g of side products. The heading compound is eluted with $CH_2Cl_2$ containing 10-15% $CH_3OH$ and distilled in high vacuum, b.p. 0.02 mm 55°-58°; $[n]D^{20}=1.5110$.

(b)
8-Methyl-8-azabicyclo[3.2.1]octylidene-3-methylenecarboxylic acid

To a solution of 22 g (113 mM) of the product of step (a) in 55 ml $CH_3OH$ are added 70.5 ml (141 mM) 2N NaOH and the mixture left overnight at room temperature. The pH of the mixture is adjusted to 10, followed by extraction with $CH_2Cl_2$ (3×). The aqueous layer is acidified to a pH 1 with dilute HCl solution and chromatographed on amberlite eluting with aqueous ammonia to give the heading compound. m.p. 189°-190° (recrystallized from methanol/ethyl acetate).

(c)
8-Methyl-8-azabicyclo[3.2.1]octylidene-3-methylenecarboxylic-acid-hydrochloride 10.6 ml oxalylchloride are slowly added dropwise at 20° to a stirred suspension of 17.8 g (98.5 mM) of the product of step (b) in 70 ml abs. $CH_2Cl_2$. The reaction mixture turns clear after ½ of the volume of oxalylchloride is added. One hour after the addition is completed the heading compound crystallizes out. The mixture is left overnight, treated with 50 ml hexane, filtered and the filter cake is washed with $CH_2Cl_2$/hexane (1:1), to give the heading compound, m.p. 156°-158° (decomp.).

(d)
Indol-3-yl-carbonyl-methylenyl-3-(8-methyl-8-azabicyclo[3.2.1]octane)

To a Grignard reagent prepared from 4.8 g (0.2M) magnesium and 12.5 ml (0.2M) methyl iodide in 100 ml abs. ether is added dropwise at boiling temperature a solution of 11.7 g indole in 30 ml abs. ether. After the addition is completed the mixture is stirred at about 28°-34° for 1 hour. The mixture is then cooled to −20° C. and treated slowly under exclusion of moisture with 23.6 g of the product of step (c). The mixture is warmed to 0° C., whereby an orange suspension results, which turns to a yellow-brown resin upon achieving ambient temperature. The reaction mixture is left overnight and then treated with aqueous $Na_2CO_3$ solution and $CH_2Cl_2$. The organic layer is dried, evaporated and chromatographed on 550 g silica gel eluting with $CH_2Cl_2$ containing 7% $CH_3OH$ and 0.4% aq. ammonia. After eluting 9.4 g of indole and side products the title compound is obtained, which upon recrystallization (2×) from $CH_3OH/H_2O$ has a m.p. 140°-142° (decomp.)

EXAMPLE 2

2-Methyl-benzothiophen-3-yl-carbonyl-methylenyl-3-(8-methyl-8-azabicyclo[3.2.1]octane)

[Compound of formula Ia, wherein A=II in 3-position; X=S; $R_1=H$; $R_2=2-CH_3$; B'=IV; X-Y is

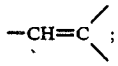

n=1; Z=H; $R_8=CH_3$]

In manner analogous to that described in Example (1d) but replacing indole with 2-methyl-benzothiophene the title compound, m.p. 89°-90° is obtained.

EXAMPLE 3

Indol-3-yl-carbonyl-methyl-3s-(8-methyl-8-azabicyclo[3.2.1]octane)

[(Compound of formula Ib, wherein A=II in 3-position; X=NH; $R_1=R_2=H$; B'=IV; X-Y is

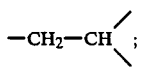

n=1; Z=H; $R_8=CH_3$]

1.4 (5 mM) of the Example 1 compound in 100 ml ethanol are hydrogenated in the presence of 1 g 10% palladium on charcoal at room temperature and normal pressure. After uptake of approximately 120 ml hydrogen (about 1 hour), the reaction mixture is filtered and concentrated, whereby the title compound crystallizes out, which is recrystallized from ethanol/water, m.p. 188°-190° (decomp.).

EXAMPLE 4

Indol-3-yl-carbonyl-methyl-3-(8-methyl-8-azabicyclo[3.2.1]oct-2,3-ene)

[Compound of formula Ic, wherein A=II in 3-position; X=NH; $R_1=R_2=H$; B'''=XII; n=1; Z=H; $R_8=CH_3$]

The Example 1 compound is heated under high vacuum (0.02 mm Hg) at 90°-95° for 18 hours, whereby an isomerization takes place. The resulting compound is purified on silica gel eluting with $CH_2Cl_2$ containing 15% $CH_3OH$ and 1% aq. ammonia, followed by recrystallization from ethanol/ethyl acetate/hexane to yield the title compound, m.p. 169°-171° (decomp.).

EXAMPLE 5

2-Methyl-benzothiophen-3-yl-carbonyl-methyl-3s-(8-methyl-8-azabicyclo[3.2.1]octane

[Compound of formula Ib, wherein A=II in 3-position; X=S; $R_1=H$; $R_2=2-CH_2$; B'=IV; X-Y is

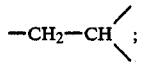

n=1; Z=H; $R_8=CH_3$]

In manner analogous to that described in Example 3 and using the Example 2 compound as starting material the title compound, m.p. 82°-83°, is obtained.

The compounds of the invention exhibit pharmacological activity and are therefore useful as pharmaceuticals, e.g. for therapy.

In particular the compounds exhibit serotonin 5-HT$_3$ receptor antagonist activity as indicated in standard tests. For example, in one test the action of the compounds in inhibiting the action of serotonin in reducing the amplitude of the compound action potential from the isolated rabbit vagus nerve was observed according to the principles of Riccioppo Neto, European Journal of Pharmacology (1978) 49 351-356, under conditions permitting differentiation between action potentials generated in myelinated nerve fibres (A fibres) and those generated in small non-myelinated fibres (C fibres) as described by B. Oakley and R. Schater, Experimental Neurobiology, A Laboratory Manual, University of Michigan Press, 1978, p. 85 to 96. Serotonin itself exerts its effect selectively on the C fibres and reduces the amplitude of the action potential in these fibres progressively with dosage. This action of serotonin is not blocked by the known serotonin antagonists, metitepine, methysergide, BOL −148, which have been said to block D receptors for serotonin, but not 5-HT$_3$ receptors (see Caddum and Picarelli, Brit. J. Pharmacol. (1957), 12, 323-328). It therefore appears that serotonin reduces the amplitude of the action potential carried by the C fibres through an effect mediated by 5-HT$_3$ receptors for serotonin which are located on these nerve fibres.

The test may be effected by establishing a dose response curve for serotonin ($10^{-7} - 5 \times 10^{-6}$M) after setting up the nerve. The serotonin is washed out and when the C fibre action potential has regained its original amplitude the compound of the invention at a set concentration of from about $10^{-16}$M to about $10^{-6}$M is preincubated with the nerve for 30 to 60 minutes. Varying concentrations of serotonin ($10^{-7}$ to $10^{-4}$M) are then applied with the compound of the invention at the concentration as was present during the preincubation period.

The 5-HT$_3$ receptor antagonists of the invention either entirely block the action of serotonin (non-competitive antagonist) or cause a parallel shift of the serotonin/dose response curve to the right (i.e. increased concentrations of serotonin were required for effect) (competitive antagonist). The pD'$_2$ or pA$_2$ value may be obtained in the conventional manner.

The 5-HT$_3$ receptor antagonist activity is also indicated by inhibiting the effect of serotonin on the isolated rabbit heart according to the method of J. R. Fozard and A. T. Moborak Ali, European Journal of Pharmacology, (1978) 49, 109-112, at concentrations of $10^{-11}$ to $10^{-5}$M of the compound of the invention. pD'$_2$ or pA$_2$ values may be calculated in the conventional manner.

The action of the compounds as 5-HT$_3$ receptor antagonists for the treatment of analgesia is confirmed by action in the hot plate test at a dose of from about 0.1 to 100 mg/kg s.c. or p.o.

The 5-HT$_3$ receptor antagonist activity is furthermore indicated in the cantharidine blister base test at a concentration of about $10^{-8}$M. A blister is produced on the skin of the forearm of human volunteers with cantharidine. When serotonin is applied to the base of such blisters it produces pain which can be measured, the intensity being proportional to the concentration of serotonin applied. The procedure has been described by C. A. Keele and D. Armstrong in "Substances producing Pain and Itch", Edward Arnold, London, 1964, p. 30 to 57. This algesic action of serotonin is not inhibited by the serotonin D receptor antagonists such as lysergic acid diethylamide or its bromo derivative and is therefore believed to be mediated by M receptors.

In the procedure followed by the area under the curve instead of the peak amplitude is measured by a linear integrater coupled to a pain intensity indicator which is operated by the volunteer. With increasing concentrations of serotonin a cumulative dose-response curve to serotonin may be obtained. When no further response on increasing the serotonin concentration is obtained, the serotonin is washed off and the blister incubated with physiological buffer solution for at least 40 minutes before the compound of the invention, is applied. The test substance is preincubated with the blister base for 30 minutes at a concentration of about $10^{-8}$M before varying concentrations of serotonin are applied. A pA$_2$ value may be obtained in the conventional manner.

The compounds of the invention are therefore useful as 5-HT$_3$ receptor antagonists, e.g. in the treatment of conditions where blockage of 5-HT$_3$-receptors would be expected to have beneficial effects, for example for the treatment of pain, especially migraine, cluster headaches and trigeminal neuralgia and also for the treatment of heart-circulation disorders, e.g. for the prevention of sudden death, and possibly as antipsychotics.

For this use the dosage will, of course, vary depending on the compound employed, mode of administration and treatment desired. However, in general, satisfactory results are obtained when administered at a daily dosage of from about 0.1 mg to about 40 mg per kg animal body weight. For the larger mammals as indicated daily dosage is in the range from about 0.5 to about 500 mg of the compound conveniently administered in divided doses 2 to 4 times a day in unit dosage form containing for example from about 0.2 mg to about 250 mg of the compound or in sustained release form.

The compounds of the invention furthermore exhibit anti-arrhythmic activity as indicated by their 5-HT$_3$ receptor antagonist activity and in standard tests. For example the compounds inhibit arrhythmias induced by norepinephrine in aneasthetized rats. In this test infusions or norepinephrine (3 to 10 microgram/kg animal body weight) are given until an arrhythmic phase as indicated by ECG measurements lasts longer than 10 seconds duration. After control of 3 consecutive injections of norepinephrine the compound of the invention is injected at doses from about 10 to about 500 microgram/kg animal body weight followed by norepinephrine injections. The arrhythmic phase is reduced, or abolished depending on the dose of test compound.

The compounds are therefore useful as anti-arrhythmic agents, e.g. in the treatment of arrhythmia. For this use the dosage will, of course, vary depending on the compound employed, mode of administration and treatment desired. However, in general, satisfactory results are obtained when administered at a daily dosage of from about 10 micrograms to about 10 milligrams per kg animal body weight. For the larger mammals an indicated daily dosage is in the range from about 0.5 to about 500 mg of the compound conveniently administered in divided doses 2 to 4 times a day in unit dosage form containing for example from about 0.2 mg to about 250 mg of the compound or in sustained release form.

Furthermore the compounds of the invention possess a benefit effect on serotonin-induced gastrointestinal disorders by action on 5-HT$_3$ receptors.

Test 1

In the following test the compounds are shown to inhibit cholera toxin-induced intestinal hypersecretion.

Method

Male NMRI mice (20-30 g) were deprivedd of food for 24 hours but had free access to water as libitum. For the duration of the experiment water was subsequently withdrawn. The test compound or saline were administered intraperitoneally. Four dose levels of each drug were investigated and each dose was given to 5 animals. One hour after pretreatment with the drug the animals were challenged with 200 μg of pure cholera toxin p.o. through a tube to the stomach followed by 2 ml of Tyrode solution. The Tyrode solution was of the following composition (mmol/l): NaCl, 137.0; CaCl$_2$, 1.8; KCl, 2.7; MgCl$_2$, 1.05; NaHCO$_3$, 11.9; NaH$_2$PO$_4$, 0.4; glucose, 5.6. Three hours later the administration of the test compound was repeated. Four hours after the cholera toxin challenge the animals were killed and the content of the whole intestine determined by weighing.

Administration protocol

| Administration protocol | |
|---|---|
| 0 hours | Administration of test compound |
| 1 hour | Administration of cholera toxin |
| 3 hours | Repeated addition of test compound |
| 4 hours | Sacrifice of animals. |

Cholera toxin usually causes a significant increase in gut weight compared to saline injection. This effect was inhibited by 50% by the test compounds, in particular by 50% at a dose of 100 to 500 μg/kg.

Test 2

In a further test the inhibition of the compounds of the invention in inhibiting the increase in gastrointestinal motility induced by B 5-hydroxytryptophan (5-HTP) was observed.

Male NMRI mice (18-32 g in weight) were fasted for 20 hours with water at libitum. The animals were separaed by a barrier from their straw and access to feces. At the beginning of the test the animals were placed in individual cages and water was removed.

All animals were treated with the test compound or saline in a volume of 0.1 ml/10 g i.p. 30 minutes later 5-HTP or saline was administered in a volume of 0.1 ml/10 g i.p. At the same time charcoal was administered p.o. (10% suspension in water; 0.1 ml/10 g). 45 minutes after the start of the experiment the animals were killed. The intestines from the stomach to the rectum were examined. For each animal the transit distance traveled by the charcoal meal along the intestine was measured. The distance was ascertained as a percentage of the whole intestinal length. For each treatment groups of at least 3 animals were used. ED$_{50}$ values were determined graphically.

The compounds of the invention inhibit 5-HTP-induced motility at doses of about 0.05 to 1 mg/kg i.v. and at doses of about 0.1 to 3.0 mg/kg p.o.

It is of interest that the compounds of the invention up to dosages of 56 mg/kg do not inhibit the not stimulated basal motility.

Test 3

The compounds of the invention facilitate field stimulation-induced contractions in muscle strips from different parts of the guinea pig stomach and are therefore indicated to increase decreased peristaltic movements in the stomach and to enhance gastric emptying in vivo. The test is effected as follows:

Male Dunkin-Hartley guinea pigs, 340-450 g, which had been starved overnight, were killed by cervical trans-section and the stomachs removed and placed in Krebs-Henseleit solution (NaCl 118.0, KCl 4.75, KH$_2$PO$_4$ 1.2, MgSO$_4$ 1.2, CaCl$_2$ 2.5, glucose 10 mM). Segments were taken from the body (approximately 20 mm long, 3-4 mm wide) with dissection in a plane suitable to investigate tension changes in the circular muscle layer. Tissues were placed in 30 ml organ baths containing oxygenated (95% O$_2$, 5% CO$_2$) Krebs-Henseleit solution at 37° C. One gram tension was applied to the tissues which were allowed to equilibrate for 45-60 min. before electrical stimulation. Intramural stimulation was achieved by using platinum wire electrodes placed approximately 5 mm apart, current being obtained from a Farnell Physiological stimulator. Tension changes were detected by Grass Tensin transducers and displayed on a multichannel Grass recorder. A frequency-response curve was initially constructed in the absence of test substance and then in the presence of the test substance which was allowed a 45 min. pretreatment time. The second curve was related to the first to assess the degree of potentiation or antagonism. Tissues were stimulated for 30 s at 5 min. intervals. Fresh tissues were used to assess such antagonist interaction. Appropriate solvent control experiments were carried out throughout the studies. Responses were measured as changes in gram tension, but to allow easier comparison between treatments, data was converted to show changes as percentage values. The significance of differences between control responses and those obtained in the presence of interacting drugs was assessed using the Mann-Whitney U test.

The compounds of the invention are active at from about $10^{-7}$M to about $10^{-9}$ Molar and induce frequency related contraction responses.

Test 4

The compounds of the invention also induce gastric emptying as indicated in standard in vivo tests, e.g. in conscious guinea pigs having stomachs made atonic (i.e. having decreased peristaltic movements) by fasting and wherein the passage of glass spheroids was observed by X-ray techniques. The experiment is effected as follows:

Food was withdrawn for 14 hours before the measurement of gastric emptying. The experiment was conducted under low illumination with minimal noise and disturbance, and was carried out only by those experimentors who had daily contact with the guinea pigs and who carried out the initial training to accustom the guinea pigs to handling. Therefore, animals were subject to minimal stress. Measurement of gastric emptying was achieved by X-ray location (50 KV, 30 mA, 0.5-0.9 s) using Kodak plates (NS-2T, 13×18 cm) of polystyrene-coated barium sulphate spheroids (approximately 30, 1 mm in diameter) which were swallowed by the guinea pigs when placed in the back of the mouth in 0.2 ml of 1% carboxymethylcellulose with 0.05 ml glycerin to initiate prompt and voluntary swallowing. The passage of the spheroids was followed for 3-4 h: during this period animals were placed in their normal housing cages and were only removed 5 min prior to X-ray (at 30-60 min. intervals) when they were placed in an individual perspex holding cage which held the animal comfortably in a stable position: the holding cage was correctly shaped (33×15 cm, and 13 cm high) to hold a 450-550 g guinea pig between foam—lined and an animal trained to entering the cage would do so and remain quiet and unstressed during the X-ray procedure. Gastric emptying was measured as the number of spheroids leaving the stomach.

Six guinea pigs were used at each dose level of drug and responses compared to those of guinea pigs receiving the appropriate vehicle. The significance of differences between drug and control responses was assessed using the Mann Whitney U test.

The compounds of the invention are active at doses of about 0.03 to about 1.0 mg/kg i.v. and at doses of about 0.1 to about 3.0 mg/kg p.o. in enhancing gastric emptying.

The effect of the compounds in increasing gastric emptying indicates an increased tonus on gastrointestinal tract.

The compounds of the invention are therefore useful in the treatment of gastrointestinal disorders which require antagonism of 5-HT$_3$ receptors, for example for the treatment of (including adjunctive treatment) or all of the following gastric secretion disturbances, gastritis, peptic ulcer, bilary dyskinesia, spastic colon, irritable bowel syndrome, Crohn's disease, colitis ulcerosa, carcinoid syndrome and diarrhea of different genesis, e.g. secreting diarrhea, bacterial-induced diarrhoea, choleraic diarrhoea, traveller's diarrhea, psychogenic diarrohea. The compounds are further useful in the treatment (including adjunctive treatment) of disorders requiring emptying, treatment of oesophageal motility disturbances, gastroesophageal and gastroduodermal reflux, achalasia, hiatus hernia, cardiain insufficieny, stomach hypotonia, pylorus hyperplasia, paralytic ileus and Hirschsprung disease.

For these indications, the exact dosage will, of course, vary depending upon the compound employed, mode of administration and treatment desired. In general satisfactory results are obtained in doses of from about 0.01 to about 10 mg/kg. For the larger primates, in particular humans, an indicated daily dosage is in the range from about 0.5 mg to about 500 mg of the compound conveniently administered in divided doses 2 to 4 times a day in unit dosge forms containing, for example, from about 0.1 mg to about 250 mg of the compound or in sustained release form. If desired the compounds may be administered in a single dose for acute therapy.

The compounds of the invention may be administered in similar manner to known standards for use in these indications. The suitable daily dosage for a particular compound will depend on a number of factors, such as its relative potency of activity.

On the basis of the activity of the compound of Example 1 in the above tests, an indicated daily dose for the compound of Example 1 is from about 5 to about 100 mg p.o. for larger primates such as humans in the serotonin (5-HT$_3$)-receptor antagonist utility.

The compounds of the invention may be administered in free base form, or in pharmaceutically acceptable salt form, e.g. suitable acid addition salts and quaternary ammonium salts. Such salts exhibit the same order of activity as the free bases. The present invention accordingly also provides a pharmaceutical composition comprising a compound of the invention, in free base form or an acid addition salt thereof or a quaternary ammonium salt thereof, in association with a pharmaceutically acceptable diluent or carrier. Such compositions may be formulated in conventional manner. The compounds may be administered by any conventional route in particular enterally preferably orally e.g. in the form of tablets or capsules, or pareterally e.g. in form of injectable solutions or suspensions.

In accordance with the foregoing the present invention also provides a compound of the invention as hereinbefore defined for use as a pharmaceutical, i.e. for use in therapy, for example: for use as a serotonin (5-HT$_3$) receptor antagonist; and especially for use in any of the specific indications hereinbefore recited in relation to such use; as wel as a method of treating analgesia, arrhythmia and gastrointestinal disorders e.g. for treating any of specific conditions hereinbefore recited in relation to such treatment, in a subject in need of such treatment, which method comprises administering to said subject an effective amount of a compound of the invention or a pharmaceutically acceptable acid addition salt or quaternary ammonium salt thereof.

In a preferred group of compounds of formula I A is a group of formula II, wherein the free bond is attached to the 3-position, X is —NH— or —S—, is hydrogen, R$_2$ is hydrogen or (C$_{1-4}$)alkyl, B is a group of formula IV, wherein n is 1, Z is hydrogen, R$_8$ is (C$_{1-4}$)alkyl, X-Y is

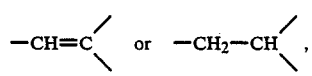

or B is a group of formula XII, wherein n is 1, Z is hydrogen and R$_8$ is (C$_{1-4}$)alkyl, as well as acid addition salts and quaternary ammonium salts thereof.

As used hereinafter a compound of formula I=a compound of the invention, especially a compound of formula I.

In accordance with the invention, it has surprisingly been found that the compounds of formula I in the form of racemates or their enantiomers are very suitable for preventing nausea and vomiting brought about by cytostatic agents, especially cisplatin, or by radio-therapy or other stimuli (e.g. medicines). This activity, especially the prevention of CIS-PLATIN EMESIS, can be deduced from the results of known tests, for example the test described by B. Costall et al. in NEUROPHARMACOLOGY 3-25, 959-961 (1986).

Furthermore, the compounds of formula I in the form of racemates or their enantiomers are suitable for suppressing travel sickness.

The doses of compounds of formula I in the form of racemates or their enantiomers, which are needed to attain the above effects, are 0.03 to ca. 1.0 mg/kg p.o. when tested on animals. The recommended daily dosage of the compounds of formula I in the form of racemates or their enantiomers in humans is ca. 0.1 to 200 mg, which is suitably administered 2 to 4 times daily in unit dosage form, containing for example ca. 0.05 to 100 mg of the compounds, optionally in sustained release form. If desired, the compounds can be used in a single dose for acute therapy.

Surprisingly it has now been found that compounds of formula I,

A—CO—B     I wherein A is a group of formula II or III,

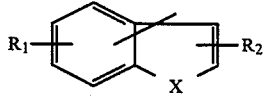

II     III wherein the free valence is attached to either fused ring in formula II, X is —$CH_2$—, —$NR_3$—, —O— or —S—, $R_1$ and $R_2$ independently are hydrogen, halogen, ($C_{1-4}$)alkyl, ($C_{1-4}$)alkoxy, hydroxy, amino, ($C_{1-4}$)alkylamino, di($C_{1-4}$)alkylamino, mercapto, or $C_{1-4}$)alkylthio, and $R_3$ is hydrogen, ($C_{1-4}$)alkyl, ($C_{3-5}$)alkenyl, aryl or aralkyl, $R_4$ to $R_7$ independently are hydrogen, amino, nitro, ($C_{1-4}$)alkylamino, di($C_{1-4}$)alkylamino, halogen, ($C_{1-4}$)alkoxy, ($C_{1-4}$)alkyl, ($C_{1-4}$)alkanoylamino or pyrrolyl, B is one of the groups of formula IV to XVIII,

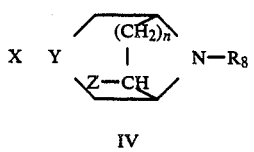

IV

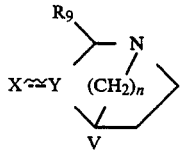

V

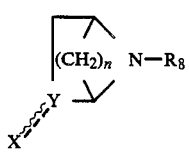

VI

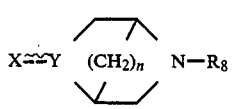

VII

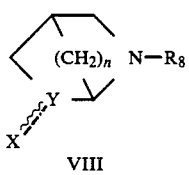

VIII

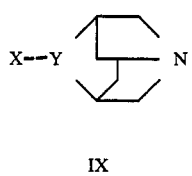

IX

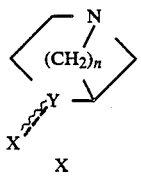

X

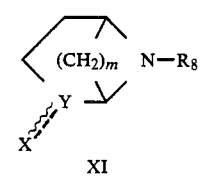

XI

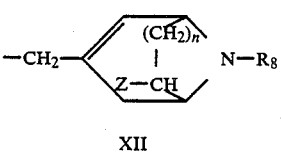

XII

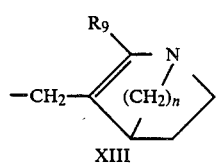

XIII

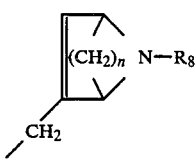

XIV

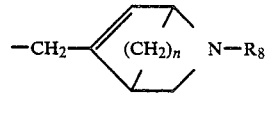

XV

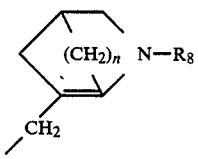

XVI

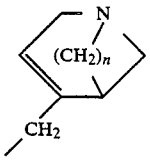

XVII

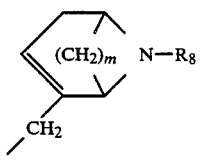

XVIII wherein
n is 1, 2 or 3,
Z is hydrogen or ($C_{1-4}$)alkoxy,
$R_8$ is hydrogen, ($C_{1-7}$)alkyl, ($C_{3-5}$)alkenyl, aryl or aralkyl and X-Y is $$-CH=C\diagup_\diagdown \quad \text{or} \quad -CH_2-CH\diagup_\diagdown \, ,$$

$R_9$ is hydrogen or ($C_{1-4}$)alkyl,
m is 2 or 3,
the bonds in groups of formulae X and XVII is in position 3 or 4, as well as acid addition salts and quaternary ammonium salts thereof exhibit behavioral activity in ethological and endocrinological tests.

One preferred group of components of formula I are those of formula Ia,

   Ia wherein A is as defined above for formula I and B' is one of the groups IV to XI, wherein n, Z, $R_8$ and m are as defined for formula I and X-Y is

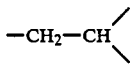

as well as acid addition salts and quaternary ammonium salts thereof.

Another preferred group of compounds of formula I are those of formula Ib,

   Ib wherein A is as defined formula I and B'' is one of the groups IV to XI, wherein n, Z, $R_8$ and m are as defined for formula I and X-Y is

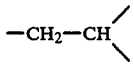

as well as acid addition salts and quaternary ammonium salts thereof.

A further preferred group of compounds of formula I are those of formula Ic,

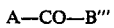   Ic wherein A is as defined for formula I, and B''' is one of the groups XII–XVIII, wherein n, Z, $R_8$ and m are as defined for formula I, as well as acid addition salts and quaternary ammonium salts thereof.

Carbonylmethylen-piperidines and -pyrrolidines e.g. compounds of formula I wherein X-Y is

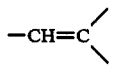

occur as a mixture of diastereoisomers (geometric cis-/trans isomers). The geometric isomers can appear as racemates as well as individual enantiomers. The compounds of the invention include all possible individual enantiomers, racemic mixtures, diastereosomers as well as mixtures thereof.

Any alkyl moiety preferably is methyl, ethyl or propyl. Alkoxy is preferably methoxy or ethoxy. Aralkyl is conveniently aryl($C_{1-4}$)alkyl. Alkenyl is preferably allyl or methallyl.

Any aryl moiety is preferably unsubstituted phenyl or phenyl mono- or poly-substituted by ($C_{1-4}$)alkyl, e.g. methyl, halogen, e.g. fluorine, hydroxy, or ($C_{1-4}$)alkoxy, e.g. methoxy. Preferably any substituted aryl group is mono-substituted. Aralkyl is conveniently benzyl. Halogen is fluorine, chlorine, bromine or iodine.

A is conveniently a group of formula II.

In the group of formula II, the carbonyl side chain may be attached to the ring carbon atom in positions 2, 3, 4, 5, 6 or 7 of the nucleus, but preferably in position 3.

Preferably A is indole.

$R_1$ is attached to the ring carbon atom in position 4, 5, 6 or 7 of the nucleus, preferably in position 5 and $R_2$ is attached to the ring carbon atom in position 2 or 3 of the nucleus. Tautomers are also covered by formula I e.g. when $R_2$ is hydroxy or mercapto in the position, $R_1$ is preferably hydrogen or halogen.

$R_2$ is preferably hydrogen or alkyl.

$R_8$ is preferably alkyl, especially methyl.

Preferred groups of formula III are of formula IIIa,

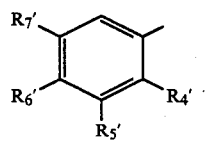   IIIa

The moiety B may have two different configurations. The two different configurations may be appreciated by making the groups have a configuration wherein a reference plane may be drawn through the carbon atoms of the ring and the nitrogen atom is above the plane and the alkylene bridge is below the plane. A group of formula IV to XVIII has the α-configuration when the group A—CO is below the plane on the same side as the alkylene bridge. This corresponds to the endo configuration and also on the configuration in troping etc. A group of formula IV to XVIII has the β-configuration when it is above the plane on the same side as the nitrogen atom. This corresponds to the exo configuration and also the configuration in pseudotropin etc. Used hereinafter is the exo/endo nomenclature. The endo isomers are preferred.

European Patent Publication No. 13138 discloses benzoic acid amides of piperidylamines having an alkylene bridge across ring positions 2 and 6. The compounds are stated to be active inter alia in increasing the intragastric pressure in the rat, in reversing the apomorphine induced delay in gastric emptying in the rat, and inhibiting the apomorphine-induced emetic effect in the rat. The compounds are indicated to be dopamine antagonists and useful in the treatment of impaired gastro-intestinal motility, such as retarded gastric emptying, dyspepsia, flatulence, esophageal reflux, peptic, ulcer and emesis.

In contrast to the compounds of the above European Patent Publication No. 13138 the compounds of the present invention in general do not significantly affect apomorphine-induced symptoms. They show on the other hand a long lasting and potent effect in the treatment of serotonin-induced psychiatric disorders by action on 5-$HT_3$ receptors. The compounds of the invention have thus a different mechanism of action to that stated for those in European Patent Publication No. 13138 and are well tolerated.

Preferred compounds of the invention include:

Indol-3-yl-carbonyl-methylenyl-3-(8-methyl-8-azabicyclo[3.2.1]octane) (hereinafter compound E) or an acid addition salt or a quaternary ammonium salt thereof.

(+)-Indol-3-yl-carbonyl-methylenyl-3-(8-methyl-8-azabicyclo[3.2.1]octane) (hereinafter compound F) or an acid addition salt or a quaternary ammonium salt thereof.

(−)-Indol-3-yl-carbonyl-methylenyl-3-(8-methyl-8-azabicyclo[3.2.1]octane) (hereinafter compound G) or an acid addition salt or a quaternary ammonium salt thereof.

The action of the compounds of the invention is shown in the following tests:

Study A

Male intruder mice show only low levels of social activity and high levels of defensive activity when introduced into the home cage of an individually housed adult male. Benzodiazepines and related drugs increase approaxh activities in this situation (Dixon 1982, Triangle 21: 95–105 (1982) Krsiak. M. Br. J. Pharmacol. 55: 141–150 (1975)). Compounds of formula I, in oral doses of 0.1 to 1 mg/kg increase approach oriented social activity.

Study B

A modification of the situation of study A involving encounters between male mice derived of food for 6 hrs, showed that compounds of formula I prolonged time spent in approach-oriented behaviours (dose range 0.01 to 1 mg/kg).

Results of Studies A and B

Show that compounds of formula I promote social interactions in situations where stressful events normally hamper this behavior.

Study C

Stretched attend postures in mice signify an ambivalent form of conflict which is inhibited by putative anxiolytics (Kaeserman HP Psychopharmacology (1986) 89: 31–37). Compounds of formula I, when given 2 hours before, reduce the duration of stretched attend postures to mice placed on a novel elevated platform. This suggest that compounds of formula I may reduce unspecific anxiety in stressful circumstances.

Study D

Mice subjected to a novel environment, i.e. transferring them from one room to another via a trolley, exhibit a rise in plasma corticosterone which are reduced by benzodiazepines and barbituates (Lahti R. A., Barsuhn C., Res. Comm. Chem. Path. Pharm. 11: 595–603, . Le Fur et al., J. Pharm. exp. Ther. 211: 305–308). Compounds of formula I reduce such stress-induced corticosterone at 1 mg/kg p.o. whilst doses from 0.1 to 0.3 increase plasma levels of this hormone.

Taken together, the results of these studies show that compounds of formula I promote approach-oriented social behavior in otherwise stressful situations. This suggests that the compounds of formula I are of use in psychiatric disorders where the treatment of anxiety, social withdrawal, affective disorders, phychoses and other stress-related illnesses is desired. The increases in corticosterone also suggest that compounds of formula I increase vigilance, thus indicating a potential use for the compounds in disorders of vigilance e.g. geriatric illnesses. Daily dosage will depend upon the type and severity of the disorder being treated but a suitable dose-range as suggested by the results of these studies would be from 0.1 to 50 mg/person/day in single or divided oral doses.

From the compounds of formula I the above compounds E, F and G are the most active.

The compounds of formula I may be administered in free base form or in pharmaceutically acceptable acid addition salt form or in a quaternary ammonium salt form. Such salts may prepared in conventional manner and are in general known. They exhibit the same order of activity as the free base form and pharmaceutical compositions comprise a compound of formula I in free base or pharmaceutically acceptable acid addition salt form or quaternary ammonium salt form in association with a pharmaceutical carrier or diluent. Such compositions may be manufactured in conventional manner.

The specific compounds mentioned herein are preferred to be administered in the salt form mentioned in published German Patent Application No. 35 45 981, e.g. compound E as the hydrochloride. The compounds F and G have previously only been disclosed in general terms as enantiomers of the compound of example 1 of the above published German Patent Application No. 35 45 981.

The compounds can be prepared as follows:

(+)-Indol-3-yl-carbonyl-methylenyl-3-(8-methyl-8-azabicyclo[3.2.1]octane)

5.3 g of the racemic Indol-3-yl-carbonyl-methylenyl-3-(8-methyl-8-azabicyclo[3.2.1]octane) (compound of example 1 of the published German Application 35 45 981) are dissolved in 30 ml ethanol under heating. Then a solution of 7.63 g of di-p-toluene-L-tartaric acid in 30 ml ethanol is added. The combined clear solutions are concentrated, then diluted with 30 ml ethyl acetate and crystallization seeds are added. The salt crystallized out. The crystals are filtered off at 20° and washed with a mixture (1:1) of ethanol and ethylacetate. The obtained tartrate of the title compound melts at 155° to 156° (decomp.), after recrystallization from 60 ml of a mixture (2:1) of ethanol and ethylacetate at 156°–157° (decomp.) $[\alpha]D^2 = -58.9°$ (c=1.6 in ethanol/water 9:1).

4.5 g of this tartrate is partitioned between an aqueous potassium-carbonate solution (20%) and a mixture of methylenechloride and ethanol (20%). The organic layer is evaporated and the title compound is crystallized from methanol/water. The melting point can not be established as the compound is transformed during heating from 130° on, $[\alpha]D^{20} = +37.8°$ (c=1.5 in ethanol).

Hydrochloride 1.4 g of the base are dissolved in 20 ml ethanol under heating. To the obtained solution 1.4 ml of 4N hydrochlorid acid are added. The obtained clear solution is diluted with ethylacetate to the double volume whereby the salt crystallizes out. The hydrochloric of the title compound is filtered off and washed. The salt has no definite melting point as the substance—due to the migration of the double bond—is transformed during heating.

$[\alpha]D^{20} =$ +15.0° (c = 1.5 in water)
+22.2° (c = 1.5 in ethanol)

(−)-Indol-3-yl-carbonyl-methylenyl-3-(8-Methyl-8-azabicyclo[3.2.1]octane

The first motherliquor of the (−)-tartrate described in the above example is evaporated and the oily residue partitioned between an aqueous potassiumcarbonate solution (20%) and methylenechloride. After evaporation of the organic layer 3.1 g of an oily base are obtained, $[\alpha]D^{20}= -28.7°$ (c=1.6 in ethanol).

The second motherliquor of the recrystallization of the (−)-tartrate according to the above example yields after partition between an aqueous potassiumcarbonate solution (20%) and methylenechloride and evaporation of the organic layer 0.2 g of an oily base,
$[\alpha]D^{20}= -2.5$ (c=1 in ethanol).

3.25 g of the combined oily substances are dissolved in 40 ml ethanol. To the obtained solution is added a solution of 4.7 g di-p-toluene-D-tartaric acid in 30 ml ethanol. The obtained clear mixture is concentrated to a volume of 50 ml environ and 40 ml ethylacetate are added. The tartrate of the title compound crystallizes out and is filtered off at 20° and washed with ethanol-/ethylacetate (1:1 mixture). The salt melts at 157° to 158° (decomp.), after recrystallization from ethanol-/ethylacetate (2:1 mixture) the melting point remains unchanged at 157° to 158° (decomp.)
$[\alpha]D^{20}= +57.4°$ (c=1.5 in ethanol-water 9:1).

The tartrate of the title compound is transformed in the base using the process described in the previous example. After recrystallization from ethanol-methanol-water the title compound has an $[\alpha]D^{20}$ value of $-38.2°$ (c=1.5 in ethanol).

Hydrochloride 1.4 g of the obtained basic title compound are suspended in 20 ml ethanol. To the suspension 1.25 ml of a 4N hydrochloric acid are added and the resulting solution is diluted with ethylacetate to the double volume. The salt crystallizes out and is filtered off after one hour standing. After washing with ethylacetate and drying at 85° in high vacuum, the hydrochloride of the title compound melts at 155° to 165° (decomp.)

$[\alpha]D^{20} = -15.1°$ (c = 1.5 in water)
$-22.6°$ (c = 1.5 in ethanol).

The compounds may be administered by any conventional route, in particular enterally, preferably orally, e.g. in the form of tablets or capsules or parenterally, e.g. in the form of injectable solutions or suspensions.

Suitable pharmaceutical carriers and diluents for oral administration include polyethylene glycol, polyvinylpyrrolidone, mannitol, lactose etc., granulating agents and disintegrating agents such as starch and alginic acid, binding agents such as starch and gelatine, and lubricating agents such as magnesium stearate, stearic acid and talc. Suspensions may contain conserving agents like ethyl p-hydroxy-benzoate and suspending agents such as methyl-cellulose, tenside etc. For parenteral forms the compositions are preferably buffered, aqueous solutions (pH between 4 and 5). The following examples illustrate the invention.

EXAMPLE 6

Tablets for oral administration

Tablets containing the constituents as specified below were produced in conventional manner and are used in the indication specified above.

| | |
|---|---|
| Compound E as free base | 15.0 mg |
| Hydroxy-propyl-cellulose | 1.2 mg |
| Corn Starch | 13.0 mg |
| Lactose | 93.7 mg |
| Silica | 0.6 mg |

-continued

| | |
|---|---|
| Magnesium stearate | 1.5 mg |
| Tablet weight | 125.0 mg |

EXAMPLE 7

Capsules for oral administration

Capsules containing the constituents as specified below are produced in conventional manner and are used in the indications specified above.

| | |
|---|---|
| Compound F as free base | 15.0 mg |
| Lactose | 29.7 mg |
| Silica | 2.3 mg |
| Magnesium stearate | 3.0 mg |
| | 50.0 mg |

EXAMPLE 8

Injection solution for i.v. administration

A composition for injection is made up in conventional manner and is used at a dose of 10 mg a day.

| | A | B | C |
|---|---|---|---|
| Compound E in form of free base | 1.0 mg | 2.0 mg | 10.0 mg |
| Acetic acid (99 to 100%)* | 1.2 mg | 0.6 mg | 0.6 mg |
| Sodium acetate 3. H$_2$O* | 1.8 mg | 3.18 mg | 3.18 mg |
| Sodium chloride | 8.0 mg | 7.5 mg | 6.5 mg |
| Water for injection to | 1.0 ml | | | pH value 4.3;
Buffer used* 1/30 molar

EXAMPLE 9

Capsules for oral administration 5 mg and 15 mg capsules (A and B respectively) containing the constituents as specified below were produced by conventional manner and are used in the indications specified above 2–4 times a day in the case of A and once a day in the case of B.

| | A | B |
|---|---|---|
| Compound G in form of hydrochloride | 5.641 mg | 16.92 mg |
| Lactose 200 mesh | 84.929 mg | 79.29 mg |
| Lactose 100 mesh | 84.43 mg | 79.29 mg |
| Corn starch | 120.00 mg | 120.00 mg |
| Silica | 1.50 mg | 1.50 mg |
| Magnesium stearate | 3.00 mg | 3.00 mg |
| | 300 mg | 300 mg |

Capsules containing other weights can be formulated in conventional manner.

The active agents in Examples 6 to 8 may be replaced by the following compounds:

2-Methyl-benzothiophen-3-yl-carbonyl-methylenyl-3-(8-methyl-8-azabicyclo[3.2.1]octane) or an acid addition salt or a quaternary ammonium salt thereof.

Indol-3-yl-carbonyl-methyl-3s-(8-methyl-8-azabicyclo[3.2.1]octane) or an acid addition salt or a quaternary ammonium salt thereof.

Indol-3-yl-carbonyl-methyl-3-(8-methyl-8-azabicyclo[3.2.1]oct-2.3-ene) or an acid addition salt or a quaternary ammonium slt thereof.

2-Methyl-benzothiophen-3-yl-carbonyl-methyl-3s-(8-methyl)-8-azabicyclo[3.2.1]octane) or an acid addition salt or a quaternary ammonium salt thereof.

We claim:

1. A compound of formula Ic:

A—CO—B'''      Ic wherein A is a group of formula II,

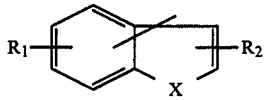

wherein the free valence is attached to either fused ring;
X is —CH$_2$—, —NR$_3$—, —O— or —S—;
R$_1$ and R$_2$ independently, are hydrogen, halogen, (C$_{1-4}$)alkyl, (C$_{1-4}$)alkoxy, hydroxy, amino, (C$_{1-4}$)alkylamino, di-(C$_{1-4}$)alkylamino, mercapto or (C$_{1-4}$)alkylthio; and
R$_3$ is hydrogen, (C$_{1-4}$)alkyl, (C$_{3-5}$)alkenyl, unsubstituted phenyl, phenyl monosubstituted by (C$_{1-4}$)alkyl, halogen, hydroxy or (C$_{1-4}$)alkoxy, or unsubstituted phenyl (C$_{1-4}$)alkyl;
or a group of formula III,

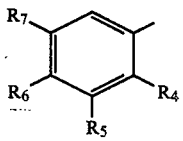

wherein
R$_4$ to R$_7$, independently, are hydrogen, amino, nitro, (C$_{1-4}$)alkylamino, di(C$_{1-4}$)alkylamino, halogen, (C$_{1-4}$)alkoxy, (C$_{1-4}$)alkyl, (C$_{1-4}$)alkanoylamino or pyrrolyl;
and B''' is one of the groups of formulae XII to XVIII,

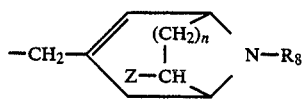

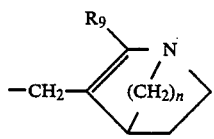

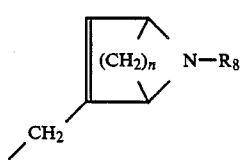

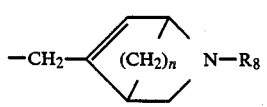

wherein
n is 1, 2 or 3;
Z is hydrogen or (C$_{1-4}$)alkoxy;
R$_8$ is hydrogen, (C$_{1-7}$)alkyl, (C$_{3-5}$)alkenyl, unsubstituted phenyl, phenyl monosubstituted by (C$_{1-4}$)alkyl, halogen, hydroxy or (C$_{1-4}$)alkoxy, or unsubstituted phenyl(C$_{1-4}$)alkyl;
R$_9$ is hydrogen or (C$_{1-4}$)alkyl;
m is 2 or 3;
and the bond in the group of formula XVII is in position 3- or 4-;
or a pharmaceutically acceptable acid addition salt or quaternary ammonium salt thereof.

2. A compound of formula I:

A—CO—B      I wherein A is a group of formula II,

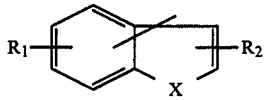

wherein the free valence is attached to the 3-position;
X is —NH— or —S—;
R$_1$ is hydrogen;
R$_2$ is hydrogen or (C$_{1-4}$)alkyl;
and B is either a group of formula IV,

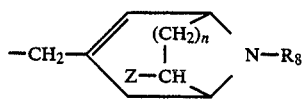

wherein
n is 1;
Z is hydrogen;
R$_8$ is (C$_{1-4}$)alkyl; and
X-Y is

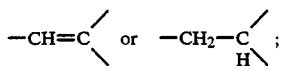

or a group of formula XII,

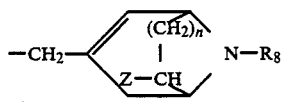

wherein n, Z and $R_8$ are as defined above;
or a pharmaceutically acceptable acid addition salt or quaternary ammonium salt thereof.

3. A compound of claim 2 which is indol-3-yl-carbonylmethylenyl-3-(8-methyl-8-azabicyclo[3.2.1]octane), or a pharmaceutically acceptable acid addition salt or quaternary ammonium salt thereof.

4. A compound of claim 2 which is 2-methyl-benzothiophen-3-yl-carbonyl-methylenyl-3-(8-methyl-8-azabicyclo[3.2.1]octane), or a pharmaceutically acceptable acid addition salt or quaternary ammonium salt thereof.

5. A compound of claim 2 which is indol-3-yl-carbonyl-methyl-3s-(8-methyl-8-azabicyclo[3.2.1]octane), or a pharmaceutically acceptable acid addition salt or quaternary ammonium salt thereof.

6. A compound of claim 2 which is indol-3-yl-carbonyl-methyl-3-(8-methyl-8-azabicyclo[3.2.1]oct-2,3-ene), or a pharmaceutically acceptable acid addition salt or quaternary ammonium salt thereof.

7. A compound of claim 2 which is 2-methyl-benzothiophen-3-yl-carbonyl-methyl-3s-(8-methyl-8-azabicyclo[3.2.1]octane), or a pharmaceutically acceptable acid addition salt or quaternary ammonium salt thereof.

8. A compound of claim 2 which is (+)-indol-3-yl-carbonylmethylenyl-3-(8-methyl-8-azabicyclo[3.2.1]octane), or a pharmaceutically acceptable acid addition salt or quaternary ammonium salt thereof.

9. A compound of claim 2 which is (−)indol-3-yl-carbonylmethylenyl-3-(8-methyl-8-azabicyclo[3.2.1]octane), or a pharmaceutically acceptable acid addition salt or quaternary ammonium salt thereof.

10. A pharmaceutical composition useful for treating algesia, arrhytmia and gastrointestinal disorders comprising a pharmaceutically acceptable carrier or diluent and a therapeutically effective amount of a compound of claim 1, or a pharmaceutically acceptable acid addition salt or quaternary ammonium salt thereof.

11. A pharmaceutical composition useful for treating algesia, arrhythmia and gastrointestinal disorders comprising a pharmaceutically acceptable carrier or diluent and a therapeutically effective amount of a compound of claim 2, or a pharmaceutically acceptable acid addition salt or quaternary ammonium salt thereof.

12. A method of treating algesia comprising administering to a subject in need of such treatment a therapeutically effective amount of a compound of claim 1, or a pharmaceutically acceptable acid addition salt or quaternary ammonium salt thereof.

13. A method for treating arrhythmia comprising administering to a subject in need of such treatment a therapeutically effective amount of a compound of claim 1, or a pharmaceutically acceptable acid addition salt or quaternary ammonium salt thereof.

14. A method of treating gastrointestinal disorders comprising administering to a subject in need of such treatment a therapeutically effective amount of a compound of claim 1, or a pharmaceutically acceptable acid addition salt or quaternary ammonium salt thereof.

15. A method of treating algesia comprising administering to a subject in need of such treatment a therapeutically effective amount of a compound of claim 2, or a pharmaceutically acceptable acid addition salt or quaternary ammonium salt thereof.

16. A method of treating arrhythmia comprising administering to a subject in need of such treatment a therapeutically effective amount of a compound of claim 2, or a pharmaceutically acceptable acid addition salt or quaternary ammonium salt thereof.

17. A method of treating gastrointestinal disorders comprising administering to a subject in need of such treatment a therapeutically effective amount of a compound of claim 2, or a pharmaceutically acceptable acid addition salt or quaternary ammonium salt thereof.

* * * * *